United States Patent [19]
von Eichborn et al.

[11] Patent Number: 5,145,677
[45] Date of Patent: * Sep. 8, 1992

[54] PROCESS FOR TREATMENT OF DISEASES

[75] Inventors: Johann-Friedrich von Eichborn, Huttisheim; Hans-Joachim Obert; Josef Brzoska, both of Laupheim, all of Fed. Rep. of Germany

[73] Assignee: Bioferon Bichemische Substanzen GmbH & Co., Laupheim, Fed. Rep. of Germany

[*] Notice: The portion of the term of this patent subsequent to Aug. 7, 2007 has been disclaimed.

[21] Appl. No.: 510,714

[22] Filed: Apr. 18, 1990

Related U.S. Application Data

[63] Continuation of Ser. No. 784,419, Oct. 4, 1985, abandoned.

[30] Foreign Application Priority Data

Oct. 5, 1984 [DE] Fed. Rep. of Germany ....... 3436637
Oct. 5, 1984 [DE] Fed. Rep. of Germany ....... 3436638
Jun. 18, 1985 [DE] Fed. Rep. of Germany ....... 3521733

[51] Int. Cl.$^5$ .............................................. A61K 37/66
[52] U.S. Cl. .................................. 424/85.5; 424/85.2; 424/85.1
[58] Field of Search ...................... 424/85.5, 85.2, 85.1

[56] References Cited

U.S. PATENT DOCUMENTS

| | | | |
|---|---|---|---|
| 4,460,574 | 7/1984 | Yabrov | 424/85 |
| 4,727,138 | 2/1988 | Goeddel | 536/27 |
| 4,840,032 | 10/1984 | Yabrov | 435/68 |
| 4,946,674 | 8/1990 | von Eichborn et al. | 424/85.5 |

FOREIGN PATENT DOCUMENTS

| | | |
|---|---|---|
| 77063A1 | 4/1983 | European Pat. Off. |
| 80032A2 | 6/1983 | European Pat. Off. |
| 87686A3 | 9/1983 | European Pat. Off. |
| 88540A3 | 9/1983 | European Pat. Off. |
| 109234A1 | 5/1984 | European Pat. Off. |
| 117470A1 | 9/1984 | European Pat. Off. |
| 128009A2 | 12/1984 | European Pat. Off. |
| 131789A2 | 1/1985 | European Pat. Off. |
| 107498A3 | 7/1985 | European Pat. Off. |
| 149551A2 | 7/1985 | European Pat. Off. |
| WO83/01198 | 4/1983 | PCT Int'l Appl. |
| 2040292 | 10/1990 | United Kingdom |

OTHER PUBLICATIONS

C. W. Czarniecki et al., "Synergistic Antiviral and Antiproliferative Activities of *Escherichia coli*—Derived Human Alpha, Beta and Gamma Interferons", *J. Virol.*, 49, pp. 490–496 (1984).
H. A. Harvey et al., "A Phase I Trial of Gamma Interferon (Hu-IFN-γ) in Advanced Malignancy", *Proc. Am. Soc. Clin. Oncol.*, 2, p. 46, (Abstract C-179), (1983).
S. J. Mora et al., "Observations on the Use of Intrathecal Interferon (IT-IFN)", *Neurology*, 34, (Suppl. 1), p. 141, (Abstract PP70), (1984).
K. Osther et al., "Human Gamma Interferon Phase I and Phase II Trails", *Proc. Am. Soc. Oncol.*, 2, p. 47 (1983).
K. Osther et al., "Phase I and Phase II Trails With Human Gamma Interferon", *The Biology of the Interferon System*, pp. 527–533 (1983).
G. Sonnenfeld, "Effects of Interferon on Antibody Formation", in *Interferon, Volume 2: Interferons and the Immune System*, J. Vilcek and E. De Maeyers, eds., Elsevier Amsterdam, pp. 95–99 (1984).
D. A. Weigent et al., "Potentiation of Lymphocyte Natural Killing Mixtures of Alpha or Beta Interferon with Recombinant Gamma Interferon", *Infection and Immunity*, 40, pp. 35–38 (1983).
R. Kurzrock et al., "Pharmacokinetics, Single Dose Tolerance and Biological Activity of Recombinant Gamma Interferon in Cancer Patients", *Cancer Res.*, 45, pp. 4167–4171 (1984).
A. Munoz et al., "Comparison of the Antiviral Action of Different Human Interferons Against DNA and RNA Viruses", *FEMS Micro. Lett.*, 21, pp. 105–111 (1984).
Niederle et al., "Phase I Study of Recombinant Human Interferon Gamma (rIFN-(gamma)) in Patients with Advanced Cancer", *Biology of the Interferon System*, p. 31 (1984).
M. Ogawa et al., "A Phase I Trail of Recombinant Interferon", *Proc. Am. Soc. Clin. Oncol.*, 4, p. 219 (1985).
van der Berg et al., "Recombinant—(gamma) (Immunneron): Results of a Phase I Trail in Patients with Cancer", *J. Biol. Resp. Mod.*, 4, pp. 264–272 (1985).
Gutterman et al., Cancer Research, 44, pp. 4164–4171, Sep. 1984.

*Primary Examiner*—Merrell C. Cashion, Jr.
*Assistant Examiner*—Choon Koh
*Attorney, Agent, or Firm*—Fish & Neave

[57] ABSTRACT

This invention relates to the treatment of various diseases such as such as those characterized by tumorigenic or neoplastic cell growth, malignant hematological systemic diseases, viral diseases, carcinomas, sarcomas, myelomas, melanomas, lymphomas, papillomas, degenerative diseases, allergic diseases, asthma, psoriasis and pain. More particularly, this invention relates to processes and compositions for treating these diseases by administering to a patient a pharmaceutically effective low dose amount of gamma interferon.

26 Claims, No Drawings

PROCESS FOR TREATMENT OF DISEASES

This is a continuation of application Ser. No. 06/784,419, filed Oct. 4, 1985, entitled Process For Treatment Of Diseases, now abandoned.

TECHNICAL FIELD OF INVENTION

This invention relates to the treatment of various malignant, non-malignant or viral diseases. More particularly, this invention relates to processes for treating diseases such as those characterized by tumorigenic or neoplastic cell growth, malignant hematological systemic diseases, viral diseases, asthma, carcinomas, sarcomas, myelomas, melanomas, lymphomas, papillomas, degenerative diseases, allergic diseases psoriasis and pain. According to this invention, low doses of natural or recombinant gamma interferons are used for the treatment of these diseases.

BACKGROUND ART

Because the precise etiology of many malignant and non-malignant diseases remains unknown, no cure for these diseases exists and effective agents are not always conventionally available for treatment of a specific disease. Such diseases have been treated, for example, by surgical techniques or by non-surgical methods including chemotherapy, radiation and therapeutics. Any value of such methods, however, is often diminished by adverse side effects or risks attendant with their use.

Therapeutics used in the treatment of such diseases fall into two classes. The first class of therapeutics, symptomatics, act on the symptoms of the disease, exerting effects both upon and throughout the total course of administration. Such symptomatics include salicylic acid, glucocorticoids and non-steroidal anti-inflammatory agents, such as inodomethacin. The second class of therapeutics act on the pathogensis of the disease, exerting their effects only after the initial weeks of administration, yet having effects lasting beyond the cessation of treatment. Such therapeutics include cortisones and immunosuppressants.

These prior therapeutic agents typically must be administered over long periods of time and are often characterized by adverse side effects. For example, those that are immunosuppressants may increase the patient's susceptibility to infection.

Interferons such as alpha interferon, beta interferon, and gamma interferon have been used as therapeutic agents in varying dosages and via several modes of administration. Generally, daily or weekly dosages of more than 20-50 million International units ("I.U.") of interferon are considered to be high, while dosages up to about 10 million I.U. are considered to be low. During the initial phase of therapeutic use, these interferons were available in small quantities which permitted the administration of dosages of less than 3 million I.U. With the development of recombinant DNA technology, however, large amounts of interferons could be produced by cloning and expression in various host/vector systems. The availability of such increased amounts of interferons led to the use of high dosages in the treatment of diseases. Since that time, dosages of less than 3 million I.U. have, as a rule, only been used in tolerance and toxicity tests or in pharmokinetic studies.

Low dose regimens of up to about 3 million I.U. of alpha or beta interferons have been reported to be ineffective for the systemic treatment of tumors and virus diseases or inferior to higher doses in those treatments. See, for example, J. M. Kirkwood and M. S. Ernstoff, "Interferons In The Treatment Of Human Cancer", *J. Clin. Oncol.*, 2, pp. 336-52 (1984); A. Billiau, *Contr. Oncol.*, 20, pp. 251-69 (1984); E. M. Bonnem and R. J. Spiegel, Interferon-α: Current Status And Future Promise", *J. Biol Resp. Modif.*, 3, pp. 580-98 (1984); T. C. Merigan et al., "Human Leukocyte Interferon For The Treatment Of Herpes Zoster In Patients Wich Cancer", *N. Engl. J. Med.*, 298, pp. 981-87 (1978); E. Heidemann et al., "Fibroblasten-Interferon zur Behandlung des Herpes Zoster" ("Fibroblast-Interferon In The Treatment Of Herpes Zoster: A Pilot Study"), *Dtsch. Med. Wschr.*, 107, pp. 695-97 (1982); S. Levin, "Clinical Use Of Interferon In Viral Infections", *Isr. J. Med. Sci.*, 19, pp. 955-58 (1983); R. L. Knobler et al., *Neurology*, 34, pp. 1273-79 (1984); M. A. Faerkkilae et al., *Act. Neur. Sci.*, 69, pp. 184-85 (1985), S. B. Greenberg and M. W. Harmon, J. A. Armstrong in P. E. Came and W. A. Carter: *Interferons and Their Applications*, Springer Verlag (1984). Only upon local treatment (intratumoral, peritumoral, intraventricular, intrathecal, intralesional, perilesional or intranasal application) have doses of less than 3 million I.U. been reported to demonstrate activity comparable to that effected by systemic application of higher doses.

In the case of the acute viral disease herpes zoster, a dose of 0.5 million I.U. alpha interferon or beta interferon per kilogram of body weight per day was reported to be acceptable, i.e. in the case of adults, about 30 million I.U. a day [T. C. Merigan, supra; E. Heidemann et al., *Onkologie*, 7, pp. 210-12 (1984)]. In the treatment of chronic viral diseases, such as chronically active hepatitis B infections, 3 to 10 million I.U. of alpha interferon or beta interferon are typically administered daily or three times a week. [R. Muller et al., *Z. Gastroenterologie*, 20, pp. 105-109 (1982); A. Billiau, supra, S. Levin, supra.] Daily doses of 6 or 200 million I.U. of alpha interferon have been administered to patients afflicted with, respectively, multiple sclerosis or amyotropic lateral sclerosis [R. L. Knobler, supra; M. A. Faerkkilae, supra].

Based on in-vitro studies, it has been reported that gamma interferon is less anti-virally active than alpha or beta interferon (see, for example, A. Munoz, L. Carrasco, *FEMS Microbiol. Letters*, 21, pp. 105-11 (1984). For this reason, gamma interferon, to date, has not been used for the systemic treatment of viral diseases.

Patients with tumors have, up to now, been treated only in phase I studies, so that no prediction as to therapeutic effectiveness of gamma interferon in these diseases is possible [S. Yamazaki, *Jpn. J. Med. Sci. Biol.*, 37, pp. 209-23 (1984); S. A. Sherwin et al., "A Preliminary Phase I Trial Of Partially Purified Interferon-γ In Patients With Cancer", *J. Biol. Resp. Modif.*, 3, pp. 599-607 (1984); J. U. Guttermann et al., "Pharmocokinetic Study Of Partially Pure γ-Interferon In Cancer", *Cancer Res.*, 44, pp. 4164-71 (1984); N. Niederle et al., in H. Kirchner and H. Schellekens (Eds.), *The Biology of the Interferon System* 1984 (1985)].

To date therefore, conventional methods and therapeutic agents have not proved to be effective in the treatment of many diseases. Accordingly, the need exists for a process which avoids the disadvantages of these conventional methods and agents while providing effective treatment for those diseases.

DISCLOSURE OF THE INVENTION

The present invention solves the problems referred to above by providing a process for the treatment of various diseases such as those characterized by tumorigenic or neoplastic cell growth, malignant hematological systemic diseases, viral diseases, carcinomas, sarcomas, myelomas, melanomas, lymphomas, papillomas, degenerative diseases, allergic diseases, psoriasis and pain. According to this invention, low doses of natural or recombinant gamma interferons are used in processes and compositions for treating such diseases. Advantageously, the processes and compositions of this invention are effective and are not beset by the variety of side effects which typically characterize conventional therapeutic treatments.

BEST MODE OF CARRYING OUT THE INVENTION

In order that the invention herein described may be more fully understood, the following detailed description is set forth.

In the description, the following terms are employed:

Gamma interferon or IFN-γ—In accordance with the interferon nomenclature announced in *Nature*, 286, p. 110 (1980) and recommended by the Interferon Nomenclature Committee in *Archives of Virology*, 77, pp. 283–85 (1983). IFN-γ was originally referred to as "immune interferon".

IFN-γ is a lyphokine which is naturally produced in minute quantities together with other lymphokines by lymphocytes. It is primarily produced by T-lymphocytes, spontaneously or in response to various inducers such as mitogens, specific antigens or specific antibodies [W. E. Stewart, II, *The Interferon System*, pp. 148–49 (1981)]. IFN-γ is a glycoprotein having a molecular weight between 20,000 and 25,000 (or 17,000 in non-glycosylated form). IFN-γ has also been cloned and expressed in various host-vector systems. The nucleotide sequence of cloned IFN-γ indicates that it is composed of 143–146 amino acids.

As used in this application and claims, "IFN-γ" includes all proteins, polypeptides and peptides which are natural or recombinant IFN-γs, or derivatives thereof, and which are characterized by the biological activity of those IFN-γs against malignant, non-malignant or viral diseases. These include IFN-γ-like compounds from a variety of sources such as natural IFN-γs, recombinant IFN-γs, and synthetic or semi-synthetic IFN-γs.

In addition, as used in this application and claims, the terms "low doses" or "low dosage" refer to doses of about $0.01-2.0 \times 10^6$ I.U. (10–200 µg) per day per $1.7M^2$ of body surface and about $0.06-1.2 \times 10^6$ I.U. (6–120 µg) per day per $M^2$ of body surface.

This invention relates to processes and compositions for treating malignant, non-malignant or viral diseases. A process according to this invention comprises the step of treating a mammal in a pharmaceutically acceptable manner with a pharmaceutically effective low dose amount of IFN-γ for a period of time sufficient to reduce the symptoms of the specific target disease.

The IFN-γs used in the processes and compositions of this invention may be produced by purification from natural sources using conventional techniques or produced by recombinant techniques.

For example, some established or transformed cell lines produce natural IFN-γ constitutively in vitro [N. Fujii et al., "Spontaneous Production of γ-Interferon In Cultures of T Lymphocytes Obtained From Patients With Behcet's Disease", *J. Immunol.*, 130, pp. 1683–86 (1983)]. A T cell hybridoma variant clone was also found to produce IFN-γ, together with other lymphokines, in response to stimulation with concanavalin A [A. Zlotnick et al., "Coordinate Production By A T Cell Hybridoma Of Gamma Interferon And Three Other Lymphokine Activities: Multiple Activities Of A Single Lymphokine?", *J. Immunol.*, 131, pp. 794–80 (1983)].

Among the IFN-γs useful in the processes of this invention are also the IFN-γs produced in vitro by a variety of cells in response to various interferon inducers. For example, these IFN-γs include IFN-γs produced in human buffy-coat leukocytes after exposure to phytohemagglutinin P, concanavalin A and staphylococcal enterotoxin A ("SEA"), M. deLey et al., "Interferon Induced In Human Leukocytes By Mitogens: Production, Partial Purification And Characterization", *Eur. J. Immunol.*, 10, pp. 877–83 (1980); in human splenocytes after stimulation with SEA, R. Devos et al., "Isolation And Characterization of IFN-Gamma mRNA Derived From Mitogen-Induced Human Splenocytes", *J. Interferon Res.*, 2, pp. 409–20 (1982); by an IL-2-independent murine T cell line after stimulation by phorbol 12-myristate 13-acetate, W. R. Benjamin et al., "Production of Immune Interferon By An Interleukin 2-Independent Murine T Cell Line", *Proc. Natl. Acad. Sci. USA*, 79, pp. 5379–83 (1982); in lymphoid cells by using calcium ionophore A-23187, F. Dianzani et al., "Human Immune Interferon: Induction in Lymphoid Cells By a Calcium Ionophore", *Infection And Immunity*, 29, pp. 561–63 (1980); and in thymocytes, G. H. Reem et al., "Gamma Interferon Induction In Human Thymocytes Activated By Lectins and B Cell Lines", *Infection And Immunity*, 37, pp. 216–21 (1982). See also, Y. R. Yip et al., "Stimulation Of Human Gamma Interferon Production By Diterpene Esters", *Infection And Immunity*, 34, pp. 131–39 (1981); U.S. Pat. Nos. 4,376,821; 4,376,822 and 4,460,685 and European patent application 63,482.

These natural IFN-γs have been subsequently purified to some extent and partially characterized. See, for example, U.S. Pat. Nos. 4,289,690, 4,314,935 and 4,382,027; European patent application 87,686; O'Malley, "Affinity Chromatography Of Human Immune Interferon", *Methods in Enzymology*, 78, pp. 540–45 (1981), and Y. K. Yip et al., "Partial Purification and Characterization of Human γ (Immune) Interferon", *Proc. Natl. Acad. Sci. USA*, 78, pp. 1601–05 (1981).

IFN-γs useful in the processes of this invention may also be produced in large amounts by cloning and expression in various host/vector systems using recombinant DNA technology. See, e.g., European patent application 88,540; R. Derynck et al., "Human Interferon γ Is Encoded By A Single Class Of mRNA", *Nucleic Acids Research*, 10, pp. 3605–13 (1982); R. Derynck et al., "Expression Of The Human Interferon-γ DNA In Yeast", *Nucleic Acids Res.*, 11, 1819–37 (1983); R. Devos et al., "In Vitro Translation And Characterization Of Human IFN-γ mRNA", *J. Clin. Hemator. Oncol.*, 11(4), p. 114 (1981); R. Devos et al., "Molecular Cloning Of Human Immune Interferon cDNA And Its Expression In Eukaryotic Cells", *Nucleic Acids Research*, 10(8), pp. 2487–501 (1982). See also, G. Simons et al., *Gene*, 28, pp. 55–64 (1984); S. J. Schaill et al., *Proc. Acad. Sci. USA*, 80, pp. 4654-58 (1983) and P. W. Gray et al., *Nature*, 295, pp. 503-08 (1982).

As a result of some of these methods, IFN-γ is present in the culture medium up to a concentration of more than 100,000 International reference units per milliliter (I.U./ml) or it is concentrated in the host itself, constituting up to 25% of the protein content of the cell.

The purification of IFN-γ from the preparations produced according to the above-described processes may be effected by means of one or a combination of the following conventional methods:

controlled pore glass (CPG) or silica gel
gel filtration (AcA 54 Sephacel S200, for example)
ion-exchange chromatography (CM-Sepharose, phospho-cellulose or DEAE-cellulose)
affinity chromatography (Con-A-Sepharose, Poly-U-Sepharose or Cu-chelate-Sepharose)
immune affinity chromatography using an anti-IFN-γ Sepharose column
HPLC (with reverse phase materials, for example).

Other purification methods are described in Y. K. Yip et al., "Partial Purification And Characterization Of Human Gamma (Immune) Interferon", *Proc. Natl. Acad. Sci. USA*, 78, pp. 1601-05 (1981), D. Novick et al., "Monoclonal Antibodies To Human Interferon-γ: Production, Affinity Purification And Radioimmunoassay", *EMBO Journal*, 2, pp. 1527-30 (1983) or West German patent DE 3136166 A1.

By means of such methods, alone or in any combination thereof, purification up to electrophoretic homogeneity is possible. While the average IFN-γ specific activity of such purified substances ranges between about 10 and 50 million International units per mg of protein, it is possible to obtain specific activities of up to 100 million to 200 million International units per mg of protein.

Clinical preparations used in the processes of this invention may contain between about 100,000 to 200,000,000 I.U. per mg of protein (1 μg of active substance contains up to 200,000 Internation reference units).

The processes and compositions of this invention may be used to treat any mammal, including humans. According to this invention, mammals are treated by the pharmaceutically acceptable administration of IFN-γ in a pharmaceutically effective low dosage and for a period of time sufficient to reduce the symptoms of the specific disease or to prevent their recurrence.

Diseases which may be treated by the processes and compositions of this invention are those characterized by tumorigenic or neoplastic cell growth, malignant hematological systemic diseases, viral diseases, carcinomas, sarcomas, myelomas, melanomas, lymphomas, papillomas, degenerative diseases, allergic diseases, asthma, psoriasis and pain. Such disease include, for example, Crohn's disease, multiple sclerosis, amyotrophic lateral sclerosis, hypernephroma, pseudomyxoma, mastocytosis, immunocytoma, Hodgkin's disease, solid tumors, Schmincke tumor, synovial sarcoma, condylomata acuminata, psoriasis vulgaris, bronchial asthma, food allergies, hepatitis B viral infections, papilloma virus infections and zoster oticus. In addition, the methods and compositions of this invention may be used for the prophylaxis of viral diseases or for recidivism prophylaxis of solid tumors and malignant hematological systemic diseases.

According to this invention, IFN-γ may be administered to the patient in any pharmaceutically acceptable dosage form, including those which may be administered to a patient intravenously as bolus or by continuous infusion over a period of minutes, hours, days, weeks or months, intramuscularly, subcutaneously, intracutaneously, intra-articularly, intrasynovially, intrathecally, periostally, or by oral, topical, or inhalation routes. IFN-γ may also be intratumorally, peritumorally, intralesionally or periolesionally administered, to exert local as well as systemic therapeutic effects.

Such dosage forms may include pharmaceutically acceptable carriers and adjuvants which are known to those of skill of the art. These carriers and adjuvants include, for example, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Adjuvants for topical or gel base forms of IFN-γ may be selected from the group consisting of sodium carboxymethylcellulose, polyacrylates, polyoxyethylene-olyoxypropylene-block polymers, polyethylene glycol and wood wax alcohols. For all administrations, conventional depot forms may be used. Such forms include, for example, microcapsules, nano-capsules, liposomes, plasters, inhalation forms, nose sprays and sublingual tablets.

The most effective mode of administration and dosage regimen of IFN-γ will depend upon the type of disease to be treated, the severity and course of that disease, previous therapy, the patient's health status and response to IFN-γ and the judgment of the treating physician. IFN-γ may be administered to the patient at one time or over a series of treatments.

Depending on the severity of the disease, a daily dose of 1.2-2 million I.U. (10-200 μg) of IFN-γ may be administered to the patient, via one or several administrations, or released from a depot form over one day, per day of treatment. For example, an initial dose of IFN-γ is administered to the patient by injection or infusion. That initial dose should contain between about 0.1 and 2 million I.U. (about 10 μg to 200 μg) of IFN-γ. For repeated administrations over several days, dosages may be administered on successive days, every two to six days, once a week, every two to four weeks or once a month, until a desired suppression of disease symptoms is observed. However, other dosage regimens are also useful. When the symptoms have been alleviated to the desired level, treatment may cease. Patients may, however, require intermittent treatment on a long term basis upon recurrence of disease symptoms.

Once improvement in the patient's condition has occurred, a maintenance dose of about 2,000,000 I.U. (approximately 200 μg) is administered about 3 times a week. Subsequently, the dosage and/or frequency of administrations is reduced, as a function of the symptoms, to a level at which the improved condition is retained. Typically, such a maintenance schedule may involve the administration of about 500,000 I.U. (approximately 50 μg) to the patient once or twice a week.

According to an alternate embodiment of this invention, the effectiveness of the IFN-γ may be increased by administration serially or in combination with other interferons derived from natural sources or produced by recombinant techniques, other cell mediators formed by leukocytes or produced by recombinant techniques such as, for example, interleukin-1, interleukin-2, tumor necrosis factor, macrophage colony stimulating factor, macrophage migration inhibitory factor, macrophage activation factor, lymphotoxin and fibroblast growth factor. Alternatively, IFN-γ may be administered serially or in combination with conventional therapeutic agents such as, for example, alkylating agents, folic acid antagonists, anti-metabolites of nucleic acid metabolism, spindle poisons, antibiotics, immune therapeutics, pyrimidine analogs, purine nucleosides, amines, triazol nucleosides, corticosteroids, calcium, antihistamines, retinoids, photosensitizing substances, lipoxygenase and cyclo-oxygenase inhibitors, fumaric acid and its salts, analgesics, psychopharmaceuticals, local anesthetics, spasmolytics, antirheumatics, calcium antagonists and beta-blockers. See, for example UICC (Ed.) in *Klinische Onkologie*, Springer-Verlag (1982); J. Fischer (Ed.), in *Taschenbuch der Onkologie*, Urban and Schwarzenberg (1983); E. De Clerq, "Specific Targets For Antiviral Drugs", *Biochem. J.*, 205, pp. 1-13 (1982); K. G. Nicholson, in *Lancet*, ii, pp. 503-06, 563-64, 617-21, 677-82 and 736-39 (1984); O. Braun-Falco et al., *Dermatologie und Venerologie*, 3d. Ed., Springer Verlag (1984); P. Nietsch, *Schmerztherapie aktuell*, Series 1-10, *Die Medizinische Welt*, 35 (1984), H. J. Senn and A. Glaus, *die Medizinische Welt*, 35, pp. 1235-40 (1984) and K. M. Foley, "The Treatment Of Cancer Pain", *N. Engl. J. Med.*, 313, pp. 84-95 (1985).

Alternatively, IFN-γ may be administered serially or in combination with radiological treatments—irradiation or introduction of radioactive substances—such as those referred to in UICC (Ed.), in *Klinische Onkologie*, Springer-Verlag (1982).

In order that the invention described herein may be more fully understood, the following examples are set forth. It should be understood that these examples are for illustrative purposes only and are not to be construed as limiting this invention in any manner.

In the following examples, the IFN-γs used in the treatment of diseases were either natural human IFN-γ or human IFN-γ produced by recombinant DNA techniques. The specific activity of the natural human IFN-γ used in the examples was in the range of 2-20×10⁶ I.U./mg of protein. Recombinant human IFN-γ was supplied by Biogen S.A., Geneva. The specific activity of Biogen's recombinant human IFN-γ was in the range of 10-20×10⁶ I.U./mg of protein.

These examples represent the results of treatment of various malignant, non-malignant and viral diseases using natural or recombinant IFN-γ according to the processes of this invention. These examples demonstrate that the administration of compositions comprising low doses of either natural or recombinant IFN-γ to patients afflicted with various such diseases effected significant and lasting decreases in or elimination of symptoms or effects of those diseases in the patients. These results, demonstrating that low doses of IFN-γ, i.e., 10-200 μg IFN-γ, were therapeutically effective and superior to higher dosages, were unexpected based upon previous clinical studies of interferons generally.

In these examples, a dose of 0.01-2.0×10⁶ I.U., or 10-200 μg, respectively, refers to a daily dose for a patient of a weight of about 60 kg and a height of about 170 cm, corresponding to about 1.7M² of body surface (Dubois and Dubois, *Arch. Intern. Med.*, 17, p. 863 (1916))—0.06-1.2×10⁶ I.U. or 6-120 μg, respectively, per M² of body surface. The individual dose for each patient was determined in corresponding manner.

EXAMPLE 1

In this example, the patient was a 57 year old male who weighed 91 kg and who was 182 cm tall. He had been suffering from hypernephroma, which had metastasized to the shaft of the humerus of the right arm, leading to extensive pain and limiting mobility of that arm.

The patient was treated with an aqueous solution comprising 100 μg/ml recombinant human IFN-γ, 5 mg human serum albumin, 8 mg sodium chloride, 0.2 mg potassium hydrogen phosphate and 1.4 gm disodium hydrogen phosphate. The concentration of IFN-γ was 100 μg/ml.

The patient received intramuscular injections of the IFN-γ composition according to the following dosage schedule and regimen:

| Treatment Week | Dosage |
| --- | --- |
| 1-2 | one injection of 100 μg four times a week |
| 3-4 | one injection of 200 μg four times a week |
| 5-6 | one injection of 400 μg four times a week |
| 7-8 | one injection of 800 μg four times a week |
| 9-10 | one injection of 1600 μg four times a week |
| 11-14 | one injection of 2100 μg once a week. |

After the first injection of IFN-γ, the amount of pain experienced by the patient was substantially decreased, while the mobility of his right arm increased considerably. After receiving the eight injection of 100 μg IFN-γ during the first week of treatment, the patient was entirely free of pain. Four days after the first injection of 2100 μg, the pain recurred.

EXAMPLE 2

In this example, the patient was a 51 year old male weighing 84 kg and who was 182 cm tall. He suffered from hypernephroma which had metastasized to the lungs and bone. The patient experienced pain in the pelvic and lumbosacral regions.

The patient was treated with a composition comprising human recombinant IFN-γ, as described in Example 1. He received intramuscular injections of the IFN-γ composition according to the following dosage regimen:

| Treatment Week | Dosage |
| --- | --- |
| 1-2 | one injection of 100 μg four times a week |
| 3-4 | one injection of 200 μg four times a week |

As a result of the treatments with 100 μg IFN-γ, the amount of pain experienced by the patient decreased substantially and continued to decrease after the third injection of 100 μg IFN-γ. After the fourth injection of 200 μg, the pain increasingly recurred.

EXAMPLE 3

In this example, the patient, a 51 year old male, weighed 84 kg and was 182 cm in height. He had been diagnosed as having hypernephroma with cutaneous pulmonary and bony metastases. The patient also suffered from psoriasis vulgaris.

The patient was treated by intramuscular injections of a composition comprising recombinant human IFN-γ and the adjuvants used in Example 1. The patient received difluoromethylornithin (DFMO) by mouth, concurrently with the IFN-γ treatment. The recombinant IFN-γ composition and the DFMO were administered to the patient according to the following regimen:

| Treatment Day | Dosage |
| --- | --- |
| 1–10 | 50 μg IFN-γ once daily and 4 g DFMO three times a day |
| 11–17 | 100 μg IFN-γ once daily and 4 g DFMO three times a day |

After seven days of treatment, the pain experienced by the patient had decreased and on day 15 of treatment, he was free of pain. As of day 12 of treatment, the symptoms of psoriasis vulgaris had decreased and had almost completely disappeared by the end of the course of therapy. At the end of the treatment period, a partial reduction of the cutaneous and liver metastases was observed. As a result of the therapy, the general condition of the patient had significantly improved.

EXAMPLE 4

In this example the patient, a 46 year old female, weighed 64 kg and was 183 cm tall. She was diagnosed as having pseudomyxoma peritonei with four fistulas in the abdominal wall.

The patient was treated with a composition comprising recombinant human IFN-γ, as described in Example 1. She received a single intramuscular injection of 100 μg of the IFN-γ composition four times a week for two weeks.

As of the third injection of IFN-γ, two out of the four fistulas in the patient's abdominal wall had closed.

EXAMPLE 5

In this example, the patient was a 59 year old male who weighed 73 kg and who was 178 cm tall. He suffered from malignant mastocytosis with diffuse bone marrow and liver infiltration and extramedullary formation of blood.

The patient was treated with a composition comprising recombinant human IFN-γ, as described in Example 1. He received intravenous injections of 50 μg of the IFN-γ composition five times a week for five weeks.

As a result of the treatment, the patient's enlarged liver had decreased in size and the alkaline phosphate level had decreased from 1700 U/l to 100 U/l (normal range is up to about t190 U/l).

EXAMPLE 6

In this example, the patient, 54 years old, suffered from progressive polymorphocellular immunocytoma, accompanied by lymphadenitis. The patient was treated with a recombinant human IFN-γ composition, as described in Example 1.

The IFN-γ composition was administered to the patient by intravenous injection of 50 μg, five times a week for four weeks.

After two weeks of therapy, the course of disease was no longer progressive and at the end of the treatment period, all lymph node swellings had regressed.

EXAMPLE 7

In this example, the patient was a male diagnosed with a fist-size skin metastasis of a malignant melanoma after surgical excision of the primary tumor. He was treated with a recombinant human IFN-γ composition as described in Example 1.

The patient received intravenous injections of 100 μg of the IFN-γ composition three to five times a week for five weeks. After three weeks of therapy, the metastasis had decreased in size by 90% and then remained stable.

EXAMPLE 8

In this example, the patient was a 50 year old male who weighed 85 kg and was 172 cm tall. He was diagnosed as having Hodgkins's disease, stage IVB, involving the liver, lung, bone marrow and abdominal lymph nodes.

The patient was treated with an aqueous solution comprising 0.1, 0.2, 0.5 or $1.0 \times 10^6$ I.U./ml natural human IFN-γ prepared from human leukocytes, 1 mg human serum albumin, 150 milli-molar sodium chloride and phosphate buffer, according to Sorensen, *Biochem Z.*, 21, p. 131 (1909) and *Biochem Z.*, 22, p. 352 (1909). the concentration of IFN-γ was $0.1–2.0 \times 10^6$/ml.

The patient received injections of the IFN-γ composition according to the following regimen:

| Treatment Day | Mode of Administration | Dosage (I.U.) |
| --- | --- | --- |
| 1 | e.c. | $0.01 \times 10^6$ |
| 2 | i.c. | $0.01 \times 10^6$ |
| 3 | s.c. | $0.01 \times 10^6$ |
| 4 | s.c. | $0.02 \times 10^6$ |
| 5 | s.c. | $0.04 \times 10^6$ |
| 6 | s.c | $0.08 \times 10^6$ |
| 7 | s.c. | $0.15 \times 10^6$ |
| 8 | s.c. | $0.3 \times 10^6$ |
| 9 | s.c. | $0.5 \times 10^6$ |
| 10 | s.c. | $1.0 \times 10^6$ |
| 11 | i.v. | $1.0 \times 10^6$ |
| 12 | i.v. | $1.0 \times 10^6$ |
| 13 | i.v. | $0.01 \times 10^6$ |
| 14 | i.v. | $0.02 \times 10^6$ |
| 15 | i.v. | $0.04 \times 10^6$ |
| 16 | i.v. | $0.08 \times 10^6$ |
| 17 | i.v. | $0.15 \times 10^6$ |
| 18 | i.v. | $0.3 \times 10^6$ |
| 19 | i.v. | $0.5 \times 10^6$ |
| 20 | i.v. | $1.0 \times 10^6$ |
| 21 | — | 0 |
| 22 | i.v. | $1.0 \times 10^6$ |

Definitions:
e.c. - extracutaneous
i.c. - intracutaneous
i.v. - intravenous
s.c. - subcutaneous At the end of the treatment period, the liver involvement had significantly regressed. In addition, the B-symptoms had improved.

EXAMPLE 9

In this example, the patient was a 61 year old male hospitalized with a Schmincke tumor with recidivism metastases to the lungs. He was treated with a composition comprising recombinant human IFN-γ, as described in Example 1. The patient received intravenous injections of $0.5 \times 10^6$ I.U. of the IFN-γ composition once a day, except on Saturdays, over a twelve week period.

This course of treatment resulted in partial remission of the extensive recidivism of the lung metastases and the patient no longer required hospitalization.

EXAMPLE 10

In this example, the patient was a 36 year old female weighing 52 kg. She was diagnosed as having synovial sarcoma accompanied by pulmonary and pleural metastases and pleural effusion. The primary tumor had been removed by amputation of the leg.

The patient was treated with a composition comprising recombinant human IFN-γ, as described in Example 1, administered by intravenous injection of 50 μg daily for fourteen days. At the end of the treatment period, the pleural effusion had resolved.

EXAMPLE 11

In this example, the patient was a male of 181 cm height and 86 kg weight, diagnosed as having carcinoma of the pancrease with liver metastases. He was treated with a composition comprising recombinant human IFN-γ, administered by intravenous injection of 100 μg daily for 3 weeks.

As of day 2 of treatment, the patient experienced a significant reduction in tumor pains and required much smaller quantities of strong analgesics.

EXAMPLE 12

In this example, the patient was a 39 year old female suffering from a chromically active hepatitis B viral injection. She was treated with a composition comprising natural human IFN-γ, as described in Example 8. The IFN-γ composition was administered to the patient by intravenous injection, five times a week for ten weeks according to the following regimen:

| Treatment Week | Dosage |
| --- | --- |
| 1 | $0.05 \times 10^6$ I.U. |
| 2-4 | $1.0 \times 10^6$ I.U. |
| 5-10 | $2.0 \times 10^6$ I.U. |

During the treatment period, the patient's DNAP, a marker for the replication of the virus, dropped from 17,422 to 5,546.

EXAMPLES 13 & 14

In these examples, two patients suffering from zoster oticus were treated. The first patient, (1), was a female whose illness as accompanied by hearing difficulties and facial paresis. The second patient, (2), was a 51 year old male whose illness was accompanied by facial paresis. The patients were treated as follows:

| Patient | Human IFN-γ Composition | Mode of Administration | Treatment |
| --- | --- | --- | --- |
| 1 | natural, prepared from human leukocytes as in Ex. 8 | i.m. injection | $0.5 \times 10^6$ I.U., twice a day for five days |
| 2 | recombinant, as in Ex. 1 | i.m. injection | 100 μg, twice a day for five days |

At the completion for the treatment period, both patients were practically cured of the zoster oticus infections and their nerve functions had returned to normal.

EXAMPLE 15

In this example, the patient was a 20 year old female, diagnosed as having condylomata acuminata. She was treated with a recombinant human IFN-γ composition as described in Example 1, receiving daily subcutaneous injections of 200 μg for seven days. As a result, the condylomas had almost completely disappeared within three weeks after the last injection.

EXAMPLE 16

In this example, the patient was a 44 year old male, weighing 57kg. He was suffering from Crohn's disease, and was treated with a natural human IFN-γ composition, as in Example 8.

The patient received injections of the IFN-γ composition over an eight week period according to the following treatment regimen:

| Treatment Week | Mode of Administration (Injection) | Dosage Per Injection |
| --- | --- | --- |
| 1 | i.m. | 0.02 to $0.1 \times 10^6$ I.U., four times a week |
| 2 | i.v. | 0.02 to $0.1 \times 10^6$ I.U., four times a week |
| 3 | i.m. | $0.1 \times 10^6$ I.U., three times a week |
| 4 | i.v. | $0.1 \times 10^6$ I.U., three times a week |
| 5 | i.m. | $0.2 \times 10^6$ I.U., three times a week |
| 6 | i.v. | $0.2 \times 10^6$ I.U., three times a week |
| 7 | i.m. | $0.5 \times 10^6$ I.U., three times a week |
| 8 | i.v. | $0.5 \times 10^6$ I.U., three times a week |

These treatments decreased the patient's Crohn index from 290 to 59.*

\* Various factors, each evaluated by points, enter into the Crohn index. These factors include, for example, number of stools, abdominal pains, general health status and weight. The higher the Crohn index, the more pronounced the disease.

EXAMPLE 17

In this example, the patient was a 38 year old male, who was 169 cm tall and weighed 53 kg. He suffered from multiple sclerosis.

He was treated with a recombinant human IFN-γ composition, as described in Example 1. The patient received subcutaneous injections of 10 μg of the IFN-γ composition 3 times a week for six weeks.

As a result of this treatment, the functions of the patient's upper and lower extremities improved and hyper-reflexia of the arms and legs had resolved. The areflexia of the epigastric region improved. The patient no longer experienced attacks of vertigo or morning stiffness.

EXAMPLE 18

In this example, the patient was a 61 year old male who was 175 cm tall and weighed 65 kg. He was suffering from amyotrophic lateral sclerosis.

The patient was treated with a recombinant human IFN-γ composition, as described in Example 1. He received intramuscular injections of the IFN-γ composition according to the following dosage schedule and regimen:

Treatment Week Dosage
1–4 one injection, three times a week, dose increasing from $0.1 \times 10^6$ to $1 \times 10^6$ I.U.
5–8 one injection of $0.5 \times 10^6$ I.U., once a week As a result of these treatments, the functions of the upper extremities improved. The patient regained the ability to flex and extend his hands, as well as to extend, flex and rotate the elbow joint to some degree. He also was able to slightly elevate the shoulder joints.

EXAMPLE 19

In this example, the patient was a 56 year old female suffering from bronchial asthma. She was treated with a natural human IFN-γ composition, as described in Example 8, administered by 3 subcutaneous injections of 100 μg over 8 days. As a result of the treatment, the patient's dyspnea was substantially reduced. The patient no longer required therapy with corticosteroids and, when required, the effective dose of theophylline was reduced by half.

EXAMPLE 20

In this example, the patient was a 43 year old female who suffered from a food allergy to oranges for several years. She was treated with a natural human IFN-γ composition, as described in Example 8. The patient received subcutaneous injections of $0.1 \times \times 10^6$ I.U. of the IFN-γ composition once a week for four weeks. As a result of this therapy, the patient's allergy was resolved after the first injection and this improvement lasted for six months after the last injection.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. A process for treating diseases characterized by tumorigenic or neoplastic cell growth, malignant hematological systemic diseases, viral diseases, asthma, carcinomas, sarcomas, myelomas, lymphomas, papillomas, Chrohn's disease, degenerative diseases, allergic diseases, psoriasis and pain comprising the step of systemically administering to a mammal a pharmaceutically effective low dosage of gamma interferon of between about 0.1 million International Units (10 μg) and 2 million International Units (200 μg) per day per $1.7M^2$ of body surface.

2. The process according to claim 1, wherein the IFN-γ is selected from the group consisting of natural IFN-γ, recombinant IFN-γ, and derivatives thereof which are characterized by the biological activity of IFN-γ against such diseases.

3. The process according to claim 1, wherein the mammal is a human.

4. The process according to claim 1, which further comprises the step of simultaneously or sequentially administering to a mammal a pharmaceutically effective amount of a compound selected from the group consisting of interferons other than IFN-γ and cell mediators formed by leukocytes.

5. The process according to claim 1, wherein the composition is administered intravenously, intramuscularly, subcutaneously, intra-articularly, intrasynovially, intrathecally, periostally, intratumorally, peritumorally, intralesionally, perilesionally, by infusion, orally, or by inhalation.

6. The process according to claim 3, wherein the low dosage is between about 0.06 million International units (6 μg) and 1.2 million International units (120 μg) per day per $M^2$ of body surface.

7. The process according to claim 4, wherein the cell mediator is selected from the group consisting of interleukin-1, interleukin-2, tumor necrosis factor, macrophage colony stimulating factor, macrophage migratory inhibitory factor, macrophage activation factor lymphotoxin and fibroblast growth factor.

8. The process according to claim 1, which further comprises the step of administering serially or in combination a pharmaceutically effective amount of a therapeutic agent selected from the group consisting of alkylating agents, folic acid antagonists, antimetabolites of nucleic acid metabolism, spindle poisons, antibiotics, immune therapeutics, pyrimidine analogs, purine nucleosides, amines, triazol nucleosides, corticosteroids, calcium, antihistamines, retinoids, photosensitizing substances, lipoxyganase and cyclo-oxygenase inhibitors, fumaric acid and its salts, analgesics, psychopharmaceuticals, local anesthetics, spasmolytics, antirheumatics, calcium antagonists, and beta-blockers.

9. A process according to claim 1, wherein the disease treated is Chron's disease.

10. A process according to claim 1, wherein the disease treated is multiple sclerosis.

11. A process according to claim 1, wherein the disease treated is amyotrophic lateral sclerosis.

12. A process according to claim 1, wherein the disease treated is renal cell carcinoma.

13. A process according to claim 1, wherein the disease treated is pseudomyxoma.

14. A process according to claim 1, wherein the disease treated is mastocytosis.

15. A process according to claim 1, wherein the disease treated is immunocytoma.

16. A process according to claim 1, wherein the disease treated is Hodgkin's disease.

17. A process according to claim 1, wherein the disease treated is melanoma.

18. A process according to claim 1, wherein the disease treated is carcinoma of the pancreas.

19. A process according to claim 1, wherein the disease treated is Schmincke tumor.

20. A process according to claim 1, wherein the disease treated is synovial sarcoma.

21. A process according to claim 1, wherein the disease treated is condylomata acuminata.

22. A process according to claim 1, wherein the disease treated is psoriasis vulgaris.

23. A process according to claim 1, wherein the disease treated is bronchial asthma.

24. A process according to claim 1, wherein the disease treated is hepatitis B viral infection.

25. A process according to claim 1, wherein the disease treated is food allergy.

26. A process according to claim 1, wherein the disease treated is zoster oticus.

* * * * *